United States Patent [19]

Vollhardt et al.

[11] 4,292,415
[45] Sep. 29, 1981

[54] NOVEL FISCHER-TROPSCH CATALYSTS

[75] Inventors: Kurt P. C. Vollhardt, Kensington; Patrick Perkins, Berkeley, both of Calif.

[73] Assignee: The United State of America as represented by the United States Department of Energy, Washington, D.C.

[21] Appl. No.: 145,187

[22] Filed: Apr. 29, 1980

Related U.S. Application Data

[62] Division of Ser. No. 39,986, May 17, 1979, Pat. No. 4,230,633.

[51] Int. Cl.$^3$ .............................. C08F 8/18; C08F 8/22
[52] U.S. Cl. ...................................... 525/357; 521/53; 521/55; 525/366
[58] Field of Search ....................... 525/357, 366, 332; 521/53, 55; 260/449.6 M, 449 M; 252/431 R

[56] References Cited

U.S. PATENT DOCUMENTS

| | | | |
|---|---|---|---|
| 4,022,810 | 5/1977 | Kobylinski et al. | 260/449.6 M |
| 4,032,556 | 6/1977 | Banks | 260/449.6 M |
| 4,096,163 | 6/1978 | Chang et al. | 260/449.6 M |
| 4,111,866 | 9/1978 | Torekai et al. | 521/55 |
| 4,128,706 | 12/1978 | Seito et al. | 521/53 |
| 4,132,672 | 1/1979 | Wise et al. | 260/449.6 M |
| 4,205,134 | 5/1980 | Seito et al. | 521/53 |
| 4,230,633 | 10/1980 | Vollhavelt et al. | 521/53 |

OTHER PUBLICATIONS

Polystyrene Attached Titanocene Species, J. Am. Chem. Soc. 97:8, Apr. 16 (1975) pp. 2128–2131.
Farrell et al., J. Org. Chem. vol. 41, #24, 3877 (1976).
Chandrasekaren et al., J. Organomet. Chem. 120–149 (1976).
Rousch et al., J. Am. Chem. 35–3888 (1970).
Gubitosa et al., J. Am. Chem. Soc. 99 (15) (1977).

*Primary Examiner*—William F. Hamrock
*Attorney, Agent, or Firm*—Harold M. Dixon; Roger S. Gaither; Richard G. Besha

[57] ABSTRACT

Novel polymer-supported metal complexes of the formula:

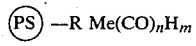

where:
- (PS) represents a divinylbenzene crosslinked polystyrene in which the divinylbenzene crosslinking is greater than 1% and less than about 18%;
- R represents a cycloalkadienyl radical of 4 through 6 carbon atoms;
- Me represents a Group VIII metal;
- CO represents a carbonyl radical;
- H represents hydrogen;
- n represents an integer varying from 0 through 3;
- m represents an integer varying from 0 through 2 inclusively with the further provision that 2n+m must total 18 when added to the electrons in R and Me, or n+m must total 0;

are prepared by:
brominating (PS)—H by treating same with bromine in the presence of a thallium salt in a partially or fully halogenated solvent to form (PS)—Br;
treating said (PS)—Br so produced with a lithium alkyl of 1 through 12 carbon atoms in an aromatic solvent to produce (PS)—Li;
substituting said (PS)—Li so produced by reaction with a 2-cycloalkenone of 4 to 6 carbon atoms in the presence of an ether solvent and using a water work-up to form a cycloalkenylalcohol-substituted (PS);
dehydrating said alcohol so produced by heating under a vacuum to produce a cycloalkadienyl-substituted (PS);
reacting the cycloalkadienyl-substituted (PS) with metal carbonyl in the presence of a partially or fully halogenated hydrocarbon, aromatic hydrocarbon of 6 through 8 carbon atoms, ethers, or esters of 4 through 10 carbon atoms as a solvent to produce a polystyrene-supported cycloalkadienyl metal carbonyl.

The novel compounds are used as improved Fischer-Tropsch catalysts particularly for the conversion of CO+H$_2$ to gaseous and liquid hydrocarbons at milder conditions than with prior catalysts.

9 Claims, No Drawings

NOVEL FISCHER-TROPSCH CATALYSTS

This is a division of application Ser. No. 39,986, filed May 17, 1979, now U.S. Pat. No. 4,230,633.

BACKGROUND OF THE INVENTION

The invention described herein was made in the course of, or under, Contract No. W-7405-ENG-48 between the U.S. Department of Energy and the University of California.

The present invention pertains to novel polystyrene-supported metal complex compounds, a process for preparing metal complex compounds, and the use of metal complex compounds in the conversion of coal. More particularly the present invention pertains to novel polystyrene-supported metal complexes wherein the metal in said complex is chemically bound to said polymer support, a process for attaching the metal in said complex to said polymer support and the use of said polymer-supported metal complex as a catalyst in carrying out Fischer-Tropsch reactions particularly in making substitute or synthetic natural gas.

It is known that the Fischer-Tropsch reaction can be used to produce a variety of products such as methane, higher hydrocarbons, and oxygenated hydrocarbons such as methanol. The product is influenced in each case by the reaction parameters which include not only the reaction pressure and temperature, but the ratio of reactants and the catalyst. One of the principal uses of Fischer-Tropsch synthesis is in the manufacture of substitute or synthetic natural gas (SNG) which consists principally of methane. The production of SNG from coal is sometimes referred to in the art as the "methanation of coal." Strictly speaking, the process involves the manufacture of SNG from carbon monoxide and hydrogen which have been derived from the gasification of coal.

"Coal gasification" is the conversion of coal, coke, or char to gaseous products by reaction with air, oxygen, steam, carbon dioxide, or a mixture thereof. Products consist of carbon dioxide, carbon monoxide, hydrogen, methane, other gases, and liquids, depending upon such parameters as the reactants employed, the use of catalysts, and the temperature and pressure within the gasification reactor.

A chemical reaction basic to virtually all coal gasification methods is the reaction of char (carbon) with water (steam) to produce carbon monoxide and hydrogen. This reaction can be shown as $$\text{Char(C)} + \text{H}_2\text{O(steam)} \rightarrow \text{CO} + \text{H}_2$$

In general, the various coal gasification processes can be characterized by the source of heat used to drive the char-gasification reaction above. A description of conventional methods for coal gasification is given in the *McGraw-Hill Encyclopedia of Science & Technology*, 1977 Edition, Volume 3, pages 248–249 (McGraw-Hill Book Company, New York).

The well-known water gas shift reaction is used to vary the ratio of the CO to hydrogen for use in subsequent reactions of interest here.

Production of methane and higher hydrocarbons from coal by the Fischer-Tropsch reaction typically employs an iron group catalyst (e.g., Fe, Co and Ni) at temperatures in the range of about 575° F. (300° C.) to 660° F. (350° C.) and pressures in the range of about 300 to 500 psi. The manufacture of oxygenated hydrocarbons such as methanol by Fischer-Tropsch involves similar operating parameters with the major difference being that substantially higher pressures (i.e., over about 2000 psi) are required than for making methane. While these processes are successful in making SNG or oxygenated hydrocarbons, the operating conditions leave considerable room for improvement. The relatively severe operating conditions mentioned involves high capital investment and power or energy consumption commensurate therewith. In addition the severe conditions present many operating problems. Accordingly, a catalyst which overcomes these disadvantages of the prior art processes is to be highly commended.

It is a principal object among the many objects of the present invention to provide novel compounds useful as catalysts which enable the Fischer-Tropsch synthesis to be achieved at mild operating temperatures and pressures.

It is a particular object of this invention to provide a Fischer-Tropsch catalyst having both soluble and insoluble characteristics so that it can be used in liquid form (i.e., in suspension in a hydrocarbon solvent) as a catalyst and yet readily separated from the solvent by physical means.

Another object of this invention is to provide a stable polymer-supported homogeneous metal complex catalyst composition.

Yet another object of this invention is to provide a catalyst which can be readily regenerated.

A particular object of the invention is to provide a methanation catalyst of the above character.

It is another principal object of the present invention to provide a process for making catalysts of the character described above.

Another and more particular object of this invention is to provide a process for preparing the methanation and other Fischer-Tropsch catalysts described above containing relatively large amounts of metal attached to said polymer support.

An additional object of this invention is to provide a process for preparing methanation and other Fischer-Tropsch catalysts having good activity.

It is still another principal object of the present invention to provide a process for carrying out the methanation of coal and other Fischer-Tropsch synthesis at mild temperatures and pressures.

These and other objects and advantages of the invention will become apparent from the following detailed description.

SUMMARY OF THE INVENTION

There are three broad aspects of the present invention:

(1) novel polymer-supported metal complexes;
(2) a process for making the complexes; and,
(3) a use for the complexes involving catalyzing Fischer-Tropsch synthesis at relatively mild conditions.

Briefly, the new compounds of this invention are compositions of the formula:

—RMe(CO)$_n$H$_m$ where:

 represents a divinylbenzene crosslinked polystyrene in which the divinylbenzene crosslinking is greater than about 1% and less than about 18%.

R represents a cycloalkadienyl radical of 4 through 6 carbon atoms;

Me represents a Group VIII metal present in an amount greater than about 3% by weight;

CO represents a carbonyl radical;

H represents hydrogen;

n represents an integer varying from 0 to 3;

m represents an integer varying from 0 through 2, with the further provision that 2n+m must total 18 when added to the number of electrons in R and Me or n+m must total 0.

Also briefly stated, the process of preparing the polymer-supported metal complexes wherein the divinylbenzene crosslinking is greater than about 1% and further described above which comprises:

brominating (PS)—H by treating same with bromine in the presence of a thallium (III) salt in a fully or partially halogenated hydrocarbon solvent to form (PS)—Br;

treating said (PS)—Br so produced with a lithium alkyl of about 1 through 12 carbon atoms in an aromatic hydrocarbon solvent of 6 through 8 carbon atoms to produce (PS)—Li;

substituting said (PS)—Li so produced by reaction with a 2-cycloalkenone of 4 through 6 carbon atoms in the presence of an ether solvent and using a water work-up to form a cycloalkenylalcohol-substituted (PS);

dehydrating said alcohol so produced by heating under a vacuum to produce a cycloalkadienyl substituted (PS) ligand;

reacting the (PS)—cycloalkadienyl ligand with metal carbonyl in the presence of a solvent selected from partially or fully halogenated hydrocarbons, aromatic hydrocarbons of 6 through 8 carbon atoms, ethers and esters of 4 through 10 carbon atoms, produce a polystyrene-supported cycloalkadienyl metal carbonyl.

The above compositions can be subjected to decarbonylation to enhance their Fischer-Tropsch activity.

The utility of the polymer-supported complexes involves conducting Fischer-Tropsch synthesis (particularly methanation) comprising:

Contacting CO and $H_2$ at a temperature in the range of about 212° F. (100° C.) to 480° F. (250° C.) and a pressure of at least about 40 psi in the presence of a catalyst composition described above in a hydrocarbon solvent. The decarbonylated compositions described above are particularly suitable catalysts for the reaction.

Detailed Description—Preferred Embodiments

The novel polystyrene-supported cycloalkadienyl metal complexes of this invention have been broadly defined above, however certain compositional embodiments are preferred.

The character of the stabilizing polystyrene support itself has a significant effect on the Fischer-Tropsch activity of the compounds when employed for that end use. Polystyrene crosslinked with about 1% divinylbenzene has been found to be unsatisfactory as a methanation catalyst. When the cross-linking agent is present in greater amounts, for example about 3%, the compound has been found to have good catalyst activity. However, at crosslinking levels of about 18 or 20% the compounds are contemplated to have poorer catalyst activity for methanation.

Accordingly, polystyrenes with more than about 1% divinylbenzene crosslinking are suitable in the Fischer-Tropsch process carried out according to the present invention. Polymers having greater than about 1% to less than about 20% of divinylbenzene crosslinking are contemplated to be generally preferred as the polymeric support ligand in this invention. Most preferred compounds include polymer ligands containing about 3% of the crosslinker. The crosslinked polystyrene polymer is preferably macroporous in character (i.e., pore size of about 100 to 900 A°). Those skilled in the art are familiar with the manner of obtaining a macroporous polymer rather than a microporous polymer.

Group VIII metals of the periodic table illustrated by Fe, Ni, Co, Rh, Ru and Ir can be used in the present invention.

Although all of the recited metals can be employed, cobalt and Rh are preferred in the compositions. The metals can be used in mixtures, that is the polymer-supported metal complexes can comprise a mixture of the metals in a catalyst composition as described herein. In some cases a mixture of catalysts containing different metals will be preferred. However, a single metal containing catalyst will be preferred in a majority of cases. Cobalt in particular is contemplated as the preferred metal. The amount or level of metal in the compositions should be as high as possible. Preferably, the amount of metal is at least 3% and for Co is about 5½ through 6% by weight.

The cycloalkadienyl moiety linking the polymeric support and the metal (Me) can contain 4 through 6 carbon atoms. Thus cyclobutadienyl (Cb), cyclopentadienyl (Cp), and hexadienyl (Ch) are suitable in the present invention. Cyclopentadienyl is contemplated as being preferred overall.

The metallated compositions when first prepared will contain at least one carbonyl moiety. Depending on the cycloalkadienyl (R) and metal (Me) selected, the structures can contain as high as three carbonyl moieties. They can contain up to 2 hydrogens. The number of carbonyls and hydrogens is determined by the number of electrons in R and Me. The total electrons of the $RMe(CO)_nH_m$ moiety must be 18. Since some metal ions and some cycloalkadienyl moieties contain an odd number of electrons, at least one hydrogen atom is required in some structures. In others, two hydrogens can take the place of one of the carbonyls. For example, cobalt contains 9 electrons and cyclopentadienyl contains 5 electrons. Carbonyl contains 2 electrons, therefore that moiety would be represented as $CpCo(CO)_2$ or $CpCo(CO)H_2$. Iron contains 8 electrons and cyclobutadienyl contains 4 electrons. Therefore, that moiety is represented by $CbFe(CO)_3$ or $CbFe(CO)_2H_2$. Rhodium, which contains 9, and Ch, which contains 4, would be represented as $ChRH(CO)_2H$. Thus m plus n added to the electrons which are in R and Me must total 18. However, as explained in detail later the complexes of this invention can be decarbonylated so that 2n+m must total 0 when added together (without the electrons of the cyclic diene moiety and the metal ion). Thus on one hand m+n+R electrons+Me electrons must either equal 18 or on the other hand 2n+m must be 0.

Before proceeding with a detailed discussion of the preparation of the compounds of the present invention, it will be helpful to point out that the final product and intermediates are reactive with air. Most, if not all, intermediates are also reactive with water, including the moisture in air. Accordingly, air should be excluded during the preparation. This can be achieved with a nitrogen or other inert blanket. The $N_2$ blanket can be employed at higher pressures but preferably is at about atmospheric or ambient pressures in all steps, except of course those carried out under vacuum.

It should also be understood that the solvents employed are quite important. They should, of course, be inert in the reactions and in any event not interfere with the reaction desired in the step where they are employed. Not only is the solvency power important, but the swelling effect on the polymer is also. Unless the solvent has sufficient swelling effect on the polymer, many reaction sites will remain protected and not react.

The polystyrene support must be first functionalized before it can be attached to the metal ion of the catalyst and impart activity to it. The first step in functionalizing the polystyrene is a bromination step. The second step involves lithiating the (PS)—Br.

These two steps are carried out by the general procedure of Farrall et al. in *J. Org. Chem.*, Vol. 41, No. 24, 3877 (1976).

The bromine ratio is the single most important parameter in this step but other features are also important. The bromine is preferably used in excess of stoichiometric based on polystyrene. The polymer beads are placed in a solvent which is inert to bromine. These solvents include the fully and partially halogenated hydrocarbons. Examples are CCl4, bromoform, ethylene dichloride, and methylene dichloride. CCl4 is preferred. The amount of solvent can vary widely but about 20 times to 50 times by weight based on polystyrene is preferred.

A thallium salt catalyst is required in the bromination reaction. Examples of types of salts suitable are the chloride, bromide, and carboxylic acid salts of thallium. Examples of specific salts are thallium acetate and thallium chloride. The amount of the catalyst is not critical but should be in the range of about 1/10 to 1/200 moles of catalyst to polystyrene.

Brominating temperatures are preferably in the range of about ambient to 80° C. (176° F.).

The lithiation is effected by reaction of the brominated polymer with an alkyl lithium of about 1 through 12 carbon atoms, preferably 1 through 6 carbon atoms. Illustrative examples are methyl lithium, hexyl lithium and dodecyl lithium. The solvent employed is an aromatic hydrocarbon of 6 through 8 carbon atoms or an ether. Examples are benzene, toluene, xylenes, and THF* with benzene being preferred. The amount of solvent varies over a wide range but the preferred range is about 10 times to 50 times based on the weight of (PS)—Br. Temperatures for this step are typically and preferably in the range of about 50° C. to 80° C. Molar ratios of reactants are based on such parameters as the amount of bromine incorporated into the polymer; however, the ratio of moles of alkyl lithium to moles of Br incorporated are typically 1/1 to 10/1, with the preferred ratios being about 3/1 to 6/1.
*THF is tetrahydrofuran The lithiated product is reacted with a 2-cycloalkenone of 4 through 6 carbon atoms in a solvent. The procedure is similar to that of Bond et al in *J. Am. Chem. Soc.*, 97, 2128 (1975) and Chandrasekaran et al in *J. Orgomet. Chem.*, 120, 49 (1976). The preferred alkenone is 2-cyclopentenone to produce, ultimately, a cyclopentadienyl ligand. Suitable solvents are ethers illustrated by THF which is also the preferred solvent. The amount of solvent used can be in the range of about 5 to 50 times by weight, with about 10 times as much preferred. Ratios of moles of 2-cycloalkenone to moles of Li incorporated are preferably about 1/1 to 2/1 and added at about −80° C.

In the water work-up of the foregoing product, water is added to the reaction without any interim separation after completion of the addition of the 2-cycloalkenone. However, the temperature is allowed to rise only to about 0° C. (it is highly exothermic). The water reacts to hydrolyze the lithium alkoxide to form an alcohol polymer ligand illustrated as follows:

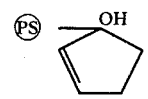

The alcohol product is dehydrated to produce a cycloalkadienyl substituent on the polymer support which is the ligand for the metal carbonyl. Dehydration is achieved by heat under vacuum. Examples of suitable temperatures of the dehydration are those in the range of about 50° C. to 100° C. Preferably the temperature of dehydration is about 70° C. The pressure under vacuum is in the range of about 0.1 to 0.001 Torr with about 0.01 to 0.001 Torr preferred. About 48 hours at 65° C. and 0.005 Torr has been found satisfactory in the laboratory. However, the temperature and pressure can be varied, within limits, to provide shorter dehydration times if desired.

The polystyrene-cycloalkadienyl metal carbonyl complex is prepared by reacting the polystyrenecycloalkadienyl ligand with the particular metal carbonyl of the metal desired. The procedure used was similar to that of Rausch et al in *J. Org. Chem.*, 35, 3888 (1970). For example in the case of cobalt, cobalt octacarbonyl is reacted with the polymeric ligand. Suitable solvents for the reaction are the halogenated hydrocarbons defined in the bromination step, the aromatic and ether solvents previously defined and organic esters. Suitable esters are those of a total of about 4 to 10 carbon atoms. Examples are ethyl acetate, butyl acetate and ethyl octanoate. Ethyl acetate is the preferred ester as contemplated. The amount of solvent relative to the cycloalkadienyl (PS) is in the range of about 5/1 to 50/1 by weight. The preferred amount of solvent is 20/1 on the same basis. The temperature varies with the particular metal carbonyl involved; however, temperatures in the range of about ambient to 50° C. (125° F.) are satisfactory. Generally preferred temperatures are about 35° C. to 45° C.

The polymer supported metal carbonyl complex can be enhanced in methanation activity by decarbonylation before use. Several methods are available to accomplish this; for example, irradiation with visible light (about 350–800 nanometers in wavelength) at a temperature of about 0° C. to 20° C. in a solvent (e.g., toluene) of vacuum pyrolysis. Vacuum pyrolysis is carried out at a temperature in the range of about 100° C. to 200° C. and a partial vacuum of about 1 to 0.001 Torr. Temperatures in the range of about 180° C. to 200° C. and partial vacua of about 0.01 to 0.001 Torr are generally preferred. Since many metal carbonyl ligands are attached to a polystyrene support, it is possible to achieve various degrees of decarbonylation on a particular polystyrene. Viewed, however, in respect to the metal, it is apparent that the number of carbonyl moieties must be a whole number or integer varying from 0 through 3 as has been previously stated. By contrast, viewed in respect to a polystyrene support, the carbonyl moiety can be a fractional number representative of the average number of carbonyls attached to the several metals on the polystyrene support.

The Fischer-Tropsch synthesis is well known in the art, however the present invention has the advantage of being able to achieve the synthesis at significantly milder conditions of both temperature and pressure. For that reason only the novel catalysts of this invention and the more desirable operating conditions will be discussed.

The new Fischer-Tropsch catalyst has an unusual catalyst character of being somewhat lipophilic and yet not actually soluble. Importantly, it forms a homogeneous compatible system with a hydrocarbon solvent. The catalyst is much like a coupling solvent or other surfactant having an apparent oil soluble portion and an insoluble portion. The importance of this combination of properties is that the catalyst can be used in a liquid form yet readily separated following its use by filtering or other facile, inexpensive physical means. But during the Fischer-Tropsch reaction which is exothermic, the liquid catalyst bath serves as an excellent heat sink for the reaction.

The solvent can be any hydrocarbon which is liquid at reaction conditions. Illustrative examples of suitable solvents are octane, benzene, toluene, and fossil fuel derived fractions. Advantageously and preferably, the solvent is a recycle stream when making liquid hydrocarbons as product.

The invention can be carried out on either a batch or continuous basis. For example it can be carried out in a countercurrent fashion of gaseous feed and solvent-catalyst. It can also be carried out using a reactor containing the liquid solvent-catalyst with a free space overhead for charging gaseous reactants. Gaseous product is recovered from the gaseous effluent and liquid product is recovered from a liquid stream withdrawn from the solvent-catalyst liquid phase with solvent being recycled to the reactor.

Broadly speaking the Fischer-Tropsch synthesis can be carried out over a relatively wide combination of reaction features including catalysts. The desired product is determinative, though, of the specific reaction features to be used. For example, the Fischer-Tropsch synthesis can be conducted at temperatures in the range of about 100° to 200° C. and at pressures in the range of about 75 to 250 psi in the presence of a cobalt catalyst to prepare SNG. Extending the reaction time results in increased amounts of higher hydrocarbons. Higher pressures are required for the synthesis of oxygenated hydrocarbons. For example pressures up to about 2000 psi is required. As contemplated, oxygenated products are preferably made at temperatures of 100° C. to 200° C. and pressures of about 1000 to 2000 psi over a rhodium catalyst.

In order to disclose more clearly the nature of the present invention and the advantages thereof, reference will hereinafter be made to certain specific embodiments which illustrate the herein-described process. It should be clearly understood, however, that this is done solely by way of example and is not to be construed as a limitation upon the spirit and scope of the appended claims.

In the examples all temperatures are °C. unless otherwise indicated.

EXAMPLE 1

Preparation of (PS)—CpCo(CO)$_2$

A. Purification of (PS)

1. (PS) crosslinked with about 3% divinylbenzene, was treated as follows to remove impurities:
    a. Resin was stirred with a solvent for about 30 minutes at the specified temperature, then filtered. Subsequent solvent was added and the process repeated.
    b. Approximate ratio of (PS) : Solvent=1:10 on a weight:volume basis, eg. 50 g (PS) :500 ml solvent.
    c. Solvent used, [number of washes](temperature), in order:
        i. CH$_2$Cl$_2$, [2], 25° C.
        ii. THF, [1], 25°
        iii. THF containing 10% by weight lithium aluminum hydride, [1], 25°
        iv. THF, [1], 25°
        v. 1 M HCl, [2], 95°–100°
        vi. 1 M KOH, [1], 70°–80°
        vii. H$_2$O, [4], 70°–80°
        viii. Dimethylformamide, [1], 40°
        ix. H$_2$O, [2], 25°
        x. 1 M HCl, [1], 80°
        xi. H$_2$O, [1], 80°xii. Methanol, [1], 25°
        xiii. 1:1 Methanol: CH$_2$Cl$_2$, [1], 25°
        xiv. 1:3 Methanol: CH$_2$Cl$_2$, [1], 25°
2. Resin was dried in vacua, 100° C., 24 hours, $2 \times 10^{-2}$ torr, then stored in sealed glass screwcap amber bottle.
3. Elemental analysis—actual (theoretical):
    %C: 92.10 (92.26)
    %H: 7.81 (7.74)
    %Al: $10^{-4}$ (0)

B. Synthesis of (PS)—Br

1. Preparation
    a. Resin dried in vacua, 80° C., 20 hrs, $10^{-2}$ Torr.
    b. Glassware dried overnight, 110° C., apparatus assembled while hot, protected from H$_2$O by CaCl$_2$.
2. Reaction
    a. 150 ml CCl$_4$ was added to a reflux apparatus (condenser, 500 ml flask, addition funnel), followed by 0.70 g finely ground Tl(OAc)$_3$ ($1.84 \times 10^{-3}$ mole).
    b. 10.17 g PS ($93.2 \times 10^{-3}$ mole styrene units) was added.
    c. Apparatus covered with black cloth to exclude light.
    d. 20 ml CCl$_4$ containing 5.4 ml Br$_2$(0.104 mole) was added slowly over one hour.
    e. Allowed reaction to stir 16 more hours at ambient temperature.
    f. Heated reaction to reflux (77° C.) for 90 minutes to complete reaction then cooled.
3. Workup
    a. Washed (PS)—Br with about 100 ml of each of the following solvents (ambient temperature)
        i. CCl$_4$
        ii. acetone
        iii. acetone: H$_2$O(2:1 by volume)
        iv. acetone
    b. Boiled (PS)—Br in (5:1 by volume) CCl$_4$: acetone to remove traces of Br$_2$, Tl(OAc)$_3$, four hours at about 60°–75°.

c. Dried (PS)—Br in vacua, 24 hrs, 80°, $2\times 10^{-2}$ Torr.

4. Elemental Analysis of (PS)—Br—Actual (theoretical):

%C: 52.49 (52.23)
%H: 3.85 (3.85)
%Br: 43.65 (43.44)

C. Synthesis of (PS)—Li and (PS)—CpOH

1. Preparation
   a. Dried apparatus capable of performing filtrations and reactions under $N_2$ atmosphere. Apparatus allows introduction and removal of solvents and reagents without exposure to the air (Schlenk glassware).
   b. All solvents and reagents dried, distilled, and degassed by standard techniques.
   c. (PS)—BR (8.37 g, $45.5\times 10^{-3}$ mole Br) placed in above apparatus and dried, 65°, 12 hrs, $10^{-3}$ Torr.
2. Reaction
   a. Under ambient pressure $N_2$, added 100 ml benzene to resin in apparatus, followed by 62 ml of a 2.2 M solution of n-butyllithium in hexane (0.136 mole, 300% of amount of Br).
   b. Heated to 65° for 3 hours, then filtered resin from solution.
   c. Repeated steps a. and b.
   d. Washed resin with 3 portions of THF, 100 ml each.
   e. Added 50 mls THF; cooled to $-78°$.
   f. Added 3.78 g 2-cyclopentenone ($46\times 10^{-3}$ mole) in 35 ml THF to $-78°$ C. reaction mixture over 2 hours.
   g. Allowed reaction to warm of its own accord to room temperature, stirred for 12 hours.
   h. Cooled to 0° C., added 50 ml ice-cold $H_2$. Stirred for 15 minutes. Filtered resin.
   i. Added 50 ml THF, then repeated step h.
   j. Repeated step i.
   k. Dried resin at room temperature, $10^{-3}$ Torr, for 24 hours.

D. Synthesis of (PS)—Cp

1. Vacuum dehydration method—sample dehydrated by gentle heating (65°–75° C.), 0.01 Torr, for 48–72 hours.
2. Acid catalyzed method—resin from above (Section C.2) was stirred with 100 ml THF and 832 mg para-toluenesulfonic acid at room temperature for 3–4 hours at room temperature under $N_2$. After reaction, resin was washed with 3 portions of THF (50 mls each) and dried in vacu (0.001 Torr, 12 hours, room temperature).

E. Synthesis of (PS)—CpCo(CO)$_2$ 1. 11.30 g $Co_2(CO)_8$ was added to about 30 mls $CH_2Cl_2$ (dry, degassed) and filtered to remove insoluble Co compounds. ($66.1\times 10^{-3}$ moles Co, about 145% mole/mole of (PS)—Br initially.
2. Resin (from Step D.2 above) was stirred with 120 ml $CH_2Cl_2$.
3. Solution from step E.1 was added to solution from step E.2.
4. Resin and $Co_2(CO)_8$ solution, contained in a reflux apparatus under $N_2$, was heated to 40° C. (boiling $CH_2Cl_2$) for 47 hours. Apparatus covered to exclude light.
5. Soxhlet extractor. Resin extracted using benzene, under $N_2$, protected from light, for 92 hours.
6. Filtered resin. Dried in vacua for 24 hours, room temperature, 0.001 Torr.
7. Elemental analysis of PS—Cp(CO)$_2$ actual:
   %C: 83.28
   H: 7.15
   Br: 0.98
   Co: 4.47
8. IR spectrum of (PS)—CpCo(CO)$_2$: two carbonyl absorptions at 2012 cm$^{-1}$ and 1954 cm$^{-1}$.

EXAMPLE 2

Preparation of (PS)—Cp-Co

A sample of (PS)—CpCo(CO)$_2$ (5 g) was heated to 190° in an evacuated flask (0.001 Torr). The rate of decarbonylation varied somewhat; decarbonylation was very slow at 100°, moderate at 160° (80% loss in 72 hours), and rapid at 190°. To insure complete decarbonylation, this and like samples were generally heated at 190° for 120 hours and showed that 98–100% of the CO had been lost.

EXAMPLE 3

Fischer-Tropsch Reaction using (PS)—CpCo(CO)$_2$

A. Preparation 1. 20 mls dry n-octane was degassed.
2. A sample of (PS)—CpCo (prepared in Example 2), 303 mg, ($2.9\times 10^{-4}$ mole Co) was placed in a glass pressure bottle. The bottle was closed with a pressure head consisting of a Viton A O-ring pressure seal, a 30" Hg. vacuum to 300 psig pressure gauge (stainless steel—SS), and two valves (SS). A teflon coated magnetic stirring bar was also included.
3. All manipulations in A.2 were performed in an $N_2$-filled glove box.

B. Reaction

1. Pressure bottle was evacuated (1 Torr pressure). 2. Pressure bottle was filled to 75 psig with $H_2$ (5 atm), then closed; no leaks were found (no pressure drop over 10 minute period).
3. Pressure was released; under flow of $H_2$, n-octane (20 mls) was added via syringe. Pressure bottle was closed and inflated to 75 psig with $H_2$. No leaks over 10 minutes.
4. Pressure was released to 52 psig, then raised to 75 psig using CO.
5. Pressure $H_2=52+15=67$ psi, pressure of $CO=23$ psi, $H_2$:CO=about 3:1.
6. No pressure change was observed upon standing for 10 minutes.
7. Heating with external oil bath with stirring was done at about 30° per minute rise in oil bath temperature.
8. External oil bath temperature was stabilized at 190°. Internal pressure rose slowly to 102 psig.
9. No real pressure change noted for 12–24 hours.
10. Pressure drop was approximately constant for next 2–5 days.
11. Cooled the pressure bottle. Pressure=51 psig at room temperature.

C. Workup and Analysis

1. Gas phase analyzed for $H_2$, CO, and $CH_4$ by gas chromatography (13X molecular sieve column).

2. Other gases (C₂H₆, C₃H₈, C₄H₁₀) in gas phase were detected on a UCW-98 column, room temperature FID) detection.

3. CH₄, C₂H₆, C₃H₈, C₄H₁₀ were verified by mass spectroscopy.

4. CH₄ was verified by IR.

5. Reaction solution was analyzed by temperature programmed GC/MS. All normal paraffins C₄–C₁₆ were present.

6. H₂O and CO₂ were found by MS analysis.

7. Resin from reaction was analyzed by IR.

8. Resin from reaction was restored to the (PS) —CpCo(CO)₂ state by use of 100 atm CO, 200° in benzene solution, 24 hours.

EXAMPLES 4–6, CONTROL 1

The procedures of Examples 3A and 3B were repeated:
Example 4:
Using D₂ instead of H₂ yielded CD₄, higher deuterocarbons, and D₂O by mass spectroscopy.
Example 5:
Using 1% DVB crosslinked (PS) —CpCo yielded only about 3% as much CH₄.
Example 6:
Repeat using (PS) CpCO(CO)₂ yielded 4% as much CH₄.
Control 1:
Repeat using (PS) and soluble CpCO(CO)₂ produced about 0.6% as much CH₄.

While particular embodiments of the invention have been described, it will be understood, of course, that the invention is not limited thereto, since many modifications may be made; and it is therefore contemplated to cover by the appended claims any such modifications as fall within the true spirit and scope of the invention.

We claim:

1. A process of preparing a polystyrene supported cycloalkadienyl metal complex of the formula:

—RMe(CO)$_n$H$_m$ where:
(PS) represents a macroporous divinylbenzene crosslinked polystyrene in which the divinylbenzene crosslinking is greater than 1% and in which the pore size is in the range of about 100 through 900 A°.
R represents a cycloalkadienyl radical of 4 through 6 carbon atoms;
Me represents a Group VIII metal;
CO represents a carbonyl radical;
H represents hydrogen;
n represents an integer varying from 0 to 3, and
m is an integer varying from 0 to 2 inclusively with the further provision that 2n+m must total 18 when added to the electrons in R and Me, or n+m must total 0, which process comprises:

brominating (PS) —H by treating same with bromine in the presence of a thallium salt in a partially or fully halogenated hydrocarbon solvent to form (PS) —Br;

treating said (PS) —Br so produced with an alkyl lithium of about 1 through 12 carbon atoms in an aromatic hydrocarbon solvent of 6 through 8 carbon atoms to produce PS —Li;

substituting said (PS) —Li so produced by reaction with a 2-cycloalkenone of 4 to 6 carbon atoms in the presence of an ether solvent and using a water work-up to form a cycloalkenylalcohol-substituted (PS);

dehydrating said alcohol so produced by heating under a vacuum to produce a cycloalkadienyl-substituted (PS);

reacting said cycloalkadienyl-substituted (PS) with metal carbonyl in the presence of a partially or fully halogenated hydrocarbon, an aromatic hydrocarbon of 6 through 8 carbon atoms, ethers and esters of 4 through 10 carbon atoms as solvent to produce a polystyrene-supported cycloalkadienyl metal carbonyl.

2. A process of preparing a polystyrene-supported cycloalkadienyl metal complex according to claim 1 where said polystyrene-supported cycloalkadienyl metal carbonyl is decarbonylated whereby n+m are 0.

3. A process of preparing a polystyrene-supported cycloalkadienyl metal complex according to claim 1 wherein R is a cyclopentadienyl radical by substituting the (PS) —Li with 2-cyclopentadienone.

4. A process of preparing a polystyrene-supported cycloalkadienyl metal complex according to claim 1 or 3 wherein Me is Co.

5. A process according to claim 1 wherein (PS) is a macroporous crosslinked polystyrene wherein the divinylbenzene crosslinking agent is present in a quantity of about 1% to 20% by weight based on polystyrene.

6. A process of preparing a polystyrene-supported metal complex according to claim 1 or 5 wherein (PS) is a macroporous crosslinked polystyrene wherein the divinylbenzene crosslinking agent is present in a quantity of about 3% by weight.

7. A process of preparing a polystyrene-supported metal complex according to claim 1 or 5 wherein (PS) is a macroporous crosslinked polystyrene wherein the divinylbenzene crosslinking agent is present in a quantity of about 3% by weight and the pore size of said macroporous polystyrene is in the range of about 100 through 900 A°.

8. A process of preparing a polystyrene-supported metal complex according to claim 1 or 7 wherein n+m are caused to be 0 by decarbonylation.

9. A process of preparing a polystyrene-supported metal complex according to claim 1 or 7 wherein n+m are caused to be 0 by decarbonylation using vacuum pyrolysis.

* * * * *